United States Patent [19]

Schönafinger et al.

[11] Patent Number: 5,424,326
[45] Date of Patent: Jun. 13, 1995

[54] PHENYL-1,2,5-OXADIAZOLECARBOXA-MIDE-2-OXIDES, THEIR PREPARATION AND THEIR USE

[75] Inventors: Karl Schönafinger, Alzenau; Helmut Bohn, Schöneck, both of Germany

[73] Assignee: Cassella Aktiengesellschaft, Frankfurt am Main, Germany

[21] Appl. No.: 66,986

[22] Filed: May 25, 1993

[30] Foreign Application Priority Data

Jun. 20, 1992 [DE] Germany .................. 42 20 264.7

[51] Int. Cl.⁶ .................. C07D 271/08; A01K 31/41
[52] U.S. Cl. .................. 514/364; 514/252; 514/256; 514/340; 544/333; 544/367; 546/277; 548/125
[58] Field of Search .............. 548/125; 514/364, 252, 514/256, 340; 544/333, 367; 540/277

[56] References Cited

U.S. PATENT DOCUMENTS

| | | | |
|---|---|---|---|
| 3,711,609 | 1/1973 | Lehmann et al. | 548/125 |
| 4,356,178 | 10/1982 | Schonafinger et al. | 548/125 |
| 4,416,893 | 11/1983 | Schonafinger et al. | 548/125 |
| 4,853,397 | 8/1989 | Sirrenberg et al. | 548/125 |

FOREIGN PATENT DOCUMENTS

| | | | |
|---|---|---|---|
| 1173034 | 8/1984 | Canada. | |
| 0075141 | 3/1983 | European Pat. Off. ... | C07D 271/08 |
| 571795 | 12/1993 | European Pat. Off. . | |
| 498137 | 12/1970 | Switzerland | C07D 85/56 |
| 498856 | 12/1970 | Switzerland | C07D 85/56 |
| 481617 | 8/1976 | U.S.S.R. | 548/125 |
| 9401422 | 1/1994 | WIPO . | |

OTHER PUBLICATIONS

"Nitric Oxide" by Burnett et al., Science, vol. 257, (1992), pp. 401–403.

"Biological Roles of Nitric Oxide" by Snyder et al., Medicine, Scientific American, May 1992, pp. 22–29.
Liebigs Ann. Chem., 1990, pp. 335–338.
Ann. Chim. (Rome) 1968, vol. 58, pp. 200–212.

*Primary Examiner*—Robert Gerstl
*Attorney, Agent, or Firm*—Perman & Green

[57] ABSTRACT

The present invention relates to phenyl-1,2,5-oxadiazolecarboxamide-2-oxides of the general formula I

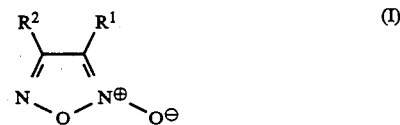

in which one of the radicals $R^1$ and $R^2$ represents

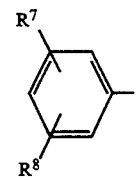

and the other represents

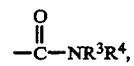

and $R^3$ and $R^4$ are defined as indicated in claim 1, to processes for their preparation and to their use for the treatment of disorders of the cardiovascular system, including angina pectoris and erectile dysfunctions.

8 Claims, No Drawings

PHENYL-1,2,5-OXADIAZOLECARBOXAMIDE-2-OXIDES, THEIR PREPARATION AND THEIR USE

BACKGROUND OF THE INVENTION

1. Field of the Invention:

The present invention relates to phenyl-1,2,5-oxadiazolecarboxamide-2-oxides, to processes for their preparation and to their use.

2. Discussion of the Prior Art:

4-Phenyl-1,2,5-oxadiazole-3-carboxamide and 3-phenyl-1,2,5-oxadiazole-4-carboxamide are already known and are described in Liebigs Ann. Chem. 1990, 335–338. The corresponding phenyl and hexyl amides are also known and are described in Ann. Chim. (Rome) 58 (1968), 200–212. However, nothing has yet been disclosed about the pharmacological properties of this class of substance.

SUMMARY OF THE INVENTION

The present invention relates to phenyl-1,2,5-oxadiazolecarboxamide-2-oxides of the formula I

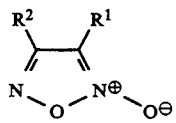
(I)

in which one of the radicals $R^1$ and $R^2$ represents

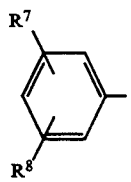

and the other represents

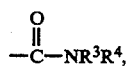

where
$R^3$ and $R^4$ independently of one another denote $(C_1-C_5)$-alkyl, $(C_5-C_7)$-cycloalkyl, $-(CH_2)_n-N:R^5R^6$, $-(CH_2)_n-OR^5$, $-(CH_2)_m-COOR^5$, $-CH(Alk)-COOR^5$, $-(CH_2)_m-CONR^5R^6$, $-CH(Alk)-CONR^5R^6$,

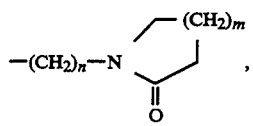

$-(CH_2)_m$-aryl or $-(CH_2)_m$-heteroaryl and $R^4$ also denotes hydrogen or $R^3$ and $R^4$, together with the nitrogen atom bonding them, form a heterocycle;
$R^5$ and $R^6$ independently of one another denote hydrogen, $(C_1-C_6)$-alkyl, $(C_5-C_7)$-cycloalkyl, benzyl or phenethyl;
Alk denotes $(C_1-C_6)$-alkyl;
n represents 2, 3 or 4 and
m represents 1, 2 or 3; and $R^7$ and $R^8$ independently of one another denote hydrogen, $(C_1-C_4)$-alkyl, $(C_1-C_4)$-alkoxy, fluorine, chlorine, bromine, nitro or trifluoromethyl;
and their pharmacologically acceptable acid addition compounds.

The $(C_1-C_6)$—, $(C_1-C_5)$— or $(C_1-C_4)$-alkyl groups representing $R^3$, $R^4$, $R^5$, $R^6$, $R^7$, $R^8$ or Alk can be straight-chain or branched. Examples are methyl, ethyl, n-propyl, i-propyl, n-butyl, i-butyl, sec-butyl, tert-butyl or hexyl. The same applies to $(C_1-C_4)$-alkoxy groups representing $R^7$ or $R^8$.

$(C_5-C_7)$-cycloalkyl representing $R^3$, $R^4$, $R^5$ or $R^6$ preferably denotes cyclopentyl or cyclohexyl.

In the $-(CH_2)_m$-aryl group representing $R^3$ or $R^4$, aryl is preferably 6- to 14-membered. Preferred $-(CH_2)_m$-aryl radicals are phenyl, benzyl and phenylethyl.

In the $-(CH_2)_m$-heteroaryl group representing $R^3$ or $R^4$, heteroaryl is preferably 5- to 7-membered and is derived, for example, from pyrrole, pyrrolidine, imidazole, pyridine, piperidine, morpholine or piperazine.

The aryl and heteroaryl groups can optionally also be monosubstituted or polysubstituted. Suitable substituents are, for example, $(C_1-C_4)$-alkyl, $(C_1-C_4)$-alkoxy, amino, $(C_1-C_4)$-alkylamino, di-$(C_1-C_4)$-alkylamino, $(C_1-C_6)$-alkanoylamino, halogen, preferably fluorine, chlorine or bromine, hydroxyl, nitro or cyano.

A heterocycle formed from $R^3$, $R^4$ and the nitrogen atom bonding them is, for example, pyrrolidine, piperidine, morpholine or piperazine, where the second nitrogen atom in the piperazine can also be substituted by a radical $R^5$.

The radicals $R^7$ and $R^8$ can be bonded in any free positions of the phenyl ring. 2,3- or 2,4-substitution is preferred.

Preferably, $R^3$ denotes $(C_1-C_5)$-alkyl and $R^4$ denotes hydrogen. It is moreover preferred if $R^3$ denotes $-(CH_2)_nN((C_1-C_6)\text{-alkyl})_2$ and $R^4$ denotes hydrogen. The

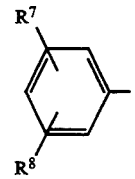

representing $R^1$ or $R^2$ preferably denotes phenyl.

Very particularly preferably $R^3$ denotes $-(CH_2)_nN((C_1-C_6)\text{-alkyl})_2$ and $R^4$, $R^7$ and $R^8$ denote hydrogen.

The compounds of the general formula I can be prepared, for example, by oxidising a compound of the general formula II

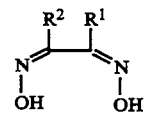
(II)

in which $R^1$ and $R^2$ are defined as indicated above.

The oxidising agents which can be employed here are conventional reagents such as, for example, halogens, alkali metal hypochlorites, lead(IV)acetate, iron(III) salts such as, for example, potassium ferricyanide, or nitrous gases, such as, for example, $N_2O_4$. The reaction is preferably carried out in a solvent, such as, for example, water, an alcohol, an ether, ethyl acetate, methylene chloride, cyclohexane, DMF, DMSO, benzene, toluene or chlorobenzene, at temperatures from −10° C. to 50° C., preferably from −5° C. to 25° C.

In the said oxidation, the compounds of the general formula I are as a rule obtained in the form of isomer mixtures. These can be separated, however, by known methods such as recrystallisation or chromatographic methods, in particular column chromatography.

Isomer mixtures are also obtained when a pure isomer is heated on its own or in an inert solvent to temperatures from 50° to 200° C. or photolysed at 0° to 50° C. By separation of the mixture obtained in this way, it is thus possible to convert one isomer into the other.

The compounds of the general formula II can be prepared by reaction of compounds of the general formula III

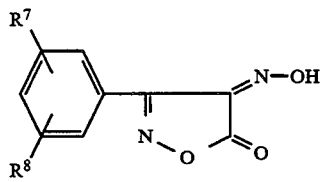
(III)

with an amine $HNR^3R^4$, where $R^3$ and $R^4$ are defined as indicated above. The reaction is preferably carried out in an inert solvent at temperatures from 0° to 50° C.

The preparation of the compound of the formula III is described in Ann. Chim. (Rome) (1968), 58(2), 189–199, and in Ann. Chim. (Rome) (1959), 49, 2083–2088.

An alternative process for the preparation of compounds of the general formula I according to the invention consists in reacting a compound of the general formula IV

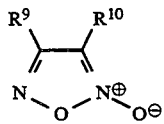
(IV)

in which one of the radicals $R^8$ and $R^{10}$ represents

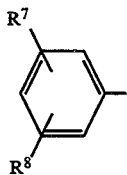

and the other represents a reactive acid group, such as, for example,

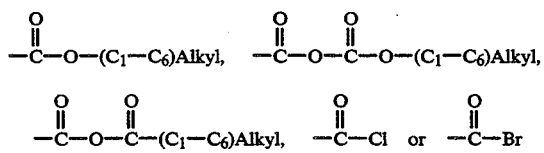

with an amine $HNR^3R^4$, in which $R^3$ and $R^4$ are defined as indicated above.

The reaction is advantageously carried out in the presence of a base which neutralises the acids formed. Preferred bases are alkali metal carbonates, such as sodium hydrogen carbonate or potassium hydrogen carbonate or sodium carbonate or potassium carbonate, alkali metal hydroxides, such as sodium hydroxide, potassium hydroxide or lithium hydroxide, alkali metal alkoxides, such as sodium methoxide or potassium methoxide, sodium ethoxide or potassium ethoxide or potassium tert-butoxide, alkali metal hydrides, such as sodium hydride or potassium hydride, alkali metal amides, such as sodium amide or lithium diisopropylamide or organic bases such as pyridine or triethylamine. These bases are preferably employed in molar amounts. Suitable solvents are, for example, ether, THF, alcohols, toluene, DMF and DMSO. The temperatures are 0° to 100° C., preferably 0° to 50° C.

If appropriate, the compounds of the general formula I according to the invention prepared by one of the processes above can be converted into other compounds of the general formula I according to the invention by modification of the substituents.

For example, the side chain —CO—NH—C(CH$_2$)$_m$COOR$^5$ can be converted by reaction with an amine HNR$^5$R$^6$ into the side chain —CO—NH—(CH$_2$)$_m$CONR$^5$R$^6$. The same is possible with the side chain —CO—NH—CH(Alk)—COOR$^5$.

By the process indicated above, compounds of the general formula Ia

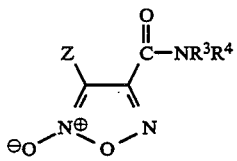
(Ia)

and of the general formula Ib

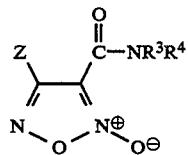
(Ib)

according to the invention, for example, can be prepared in which Z in each case represents phenyl, 2-, 3- or 4-methoxyphenyl or 3,4-dimethoxyphenyl and —NR$^3$R$^4$ in each case represents: —NH$_2$; —NHCH$_3$; —NHCH$_2$CH$_3$; —NH(CH$_2$)$_2$CH$_3$; —NH(CH$_2$)$_3$CH$_3$; —NH(CH$_2$)$_4$CH$_3$; —NH(CH$_2$)$_5$CH$_3$; —NHcycloC$_6$H$_{11}$; —NHcycloC$_5$H$_9$; —NH(CH$_2$)$_2$N(CH$_3$)$_2$; —NH—(CH$_2$)$_2$N(CH$_2$CH$_3$)$_2$; —NH(CH$_2$)$_2$N(CH$_2$CH$_2$CH$_2$CH$_3$)$_2$; —NH(CH$_2$)$_2$N(CH(CH$_3$)$_2$)$_2$; —NH(CH$_2$)$_2$NHCH(CH$_3$)$_2$; —NH(CH$_2$)$_2$NHcycloC$_6$H$_{11}$; —NH(CH$_2$)$_3$N(CH$_2$CH$_3$)$_2$;

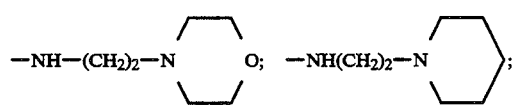

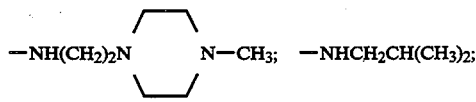

-continued

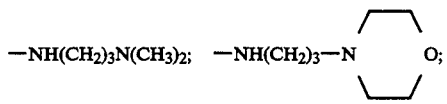

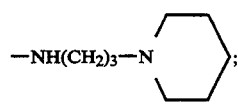

—NHCH₂C(CH₃)₃;  —NH(CH₂)₄N(CH₃)₂;
—NH(CH₂)₃NHcycloC₆H₁₁;
—NH(CH₂)₃NHC(CH₃)₃;  —NH(CH₂)₂OCH₃;
—NH(CH₂)₂OCH₂CH₃;  —NH(CH₂)₂O(OH₂)CH₃;
—NH(CH₂)₂OCH(CH₃)₂;  —NH((CH₂)₃OCH₃;
—NH(CH₂)₄OCH₃;  —NH(CH₂)₃OCH₂CH₃;
—NH(CH₂)₃O(CH₂)₃CH₃;  —NH(CH₂)₂OH;
—NH(CH₂)₃OH;  —NH(CH₂)₂OcycloC₅H₉;
—NH(CH₂)₂phenyl; —NHCH₂phenyl; —NH(CH₂)₃-phenyl;  —NH(CH₂)₂(3,4-di-OCH₃-phenyl);
—NHCH₂(4-OCH₃-phenyl);  —NHCH₂COOCH₃;
—NHCH₂COOCH;  —NHCH₂COOCH₂CH₃;
—NHCH₂CONH₂; —NHCH₂CONHCH₃; —NHCH₂CON(CH₂CH₃)₂; —NH(CH₂)₂COOH; —NH(CH₂)₂COOCH(CH₃)₂;  —NH(CH:₂)₂CONHCH₂CH₃;
—NH(CH₂)₃COOH; —NH(CH₂)₃CONH(CH₂)₃CH₃;
—NH(CH₂)₃CONH₂;  —NH(CH₂)₃COOCH₂CH₃;
—NHCH₂(3-pyridyl);  —NH(CH₂)₂(4-pyridyl);
—NH(CH₂)₂(4-imidazolyl);  —NHCH₂(2-pyridyl);
—NHCH(CH₃)COOH; —NHCH(CH(CH₃)₂)CONH₂;
—NHCH(CH₂CH(CH₃)₂)CON(CH₃)₂;
—NH(CH₂)₂(2-oxopyrrolidin-1-yl) or —NH(CH₂)₃(2-oxopyrrolidin-1-yl).

Compounds of the general formula I according to the invention which contain a basic group can form salts with inorganic or organic acids. Suitable acids for the formation of pharmacologically acceptable acid addition salts are, for example: hydrogen chloride, hydrogen bromide, naphthalene-disulphonic acids, in particular 1,5-naphthalenedisulphonic acid, phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulfamic, phenylpropionic, gluconic, ascorbic, isonicotinic, methane-sulphonic, p-toluenesulphonic, citric or adipic acid. The acid addition salts can be prepared in the customary manner by combination of the components, expediently in a suitable solvent or diluent.

The compounds of the general formula I and their pharmacologically acceptable acid addition salts have useful pharmacological properties. In the guinea-pig potassium-depolarised pulmonary artery model, they lead at low concentrations to a long-lasting relaxation. This action can be inhibited by oxyhaemoglobin, which points to an NO-mediated mechanism. Nitrogen monoxide leads, as an activator of guanylate cyclase, to an increase in cyclic guanosine monophosphate, which causes a relaxation in the smooth muscle and antiadhesive and antiaggregatory actions in the blood platelets. Nitrogen monoxide is additionally also crucially involved in learning processes, in the regulation of kidney function, in immune defence, in septic shock and in erectile dysfunctions. The compounds according to the invention can thus be employed in the said indications. Above all, however, NO donors have proven suitable for the treatment and prophylaxis of angina pectoris.

Compounds according to general formula I, in which $R^3$ and $R^4$ denote hydrogen or $R^3$ denotes hexyl or phenyl and $R^4$ denotes hydrogen, have in fact already been described as such, as indicated above, however to date nothing is known about their pharmacological properties. It has now been found that these compounds have the same pharmacological properties as the compounds of the general formula I. They can be prepared analogously to the processes indicated above.

The compounds of the general formula I

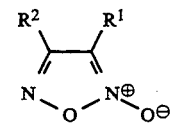

in which one of the radicals $R^1$ and $R^2$ represents

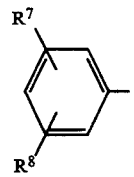

and the other represents

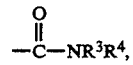

where
$R^3$ and $R^4$ independently of one another denote hydrogen, $(C_1-C_6)$-alkyl, $(C_5-C_7)$-cycloalkyl, —$(CH_2)_n$—$NR^5R^6$, —$(CH_2)_n$—$OR^5$, —$(CH_2)_m$—$COOR^5$, —CH(Alk)—$COOR^5$, —$(CH_2)_m$—$CONR^5R^6$, —CH(Alk)—$CONR^5R^6$,

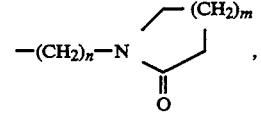

—$(CH_2)_m$-aryl or —$(CH_2)_m$-heteroaryl or phenyl or $R^3$ and $R^4$, together with the nitrogen atom bonding them, form a heterocycle;
$R^5$ and $R^6$ independently of one another denote hydrogen, $(C_1-C_6)$-alkyl, $(C_5-C_7)$-cycloalkyl, benzyl or phenethyl;
Alk denotes $(C_1-C_6)$-alkyl;
n represents 2, 3 or 4 and
m represents 1, 2 or 3; and
$R^7$ and $R^8$ independently of one another denote hydrogen, $(C_1-C_4)$-alkyl, $(C_1-C_4)$-alkoxy, fluorine, chlorine, bromine, nitro or trifluoromethyl and their pharmacologically acceptable acid addition salts can therefore be administered in humans as medicines per se, in mixtures with one another or in the form of pharmaceutical preparations which permit enteral or parenteral use and which as active constituent contain an effective dose of at least one compound of the general formula I or of an acid addition salt thereof, in addition to customary pharmaceutically innocuous excipients and additives.

The medicines can be administered orally, for example in the form of pills, tablets, coated tablets, sugar-coated tablets, hard and soft gelatin capsules, solutions, syrups, emulsions or suspensions, or aerosol mixtures. However, administration can also be carried out rectally, for example in the form of suppositories, or parenterally, for example in the form of injection solutions, or percutaneously, for example in the form of ointments or tinctures.

For the production of the pharmaceutical preparations, pharmaceutically inert inorganic or organic excipients can be used. For the preparation of pills, tablets, sugar-coated tablets and hard gelatin capsules, lactose, maize starch or derivatives thereof, talc, stearic acid or its salts, etc., for example, can be used. Excipients for soft gelatin capsules and suppositories are, for example, fats, waxes, semi-solid and liquid polyols, natural or hardened oils, etc. Suitable excipients for the production of solutions and syrups are, for example, water, sucrose, invert sugar, glucose, polyols, etc. Suitable excipients for the production of injection solutions are, for example, water, alcohols, glycerol, polyols or vegetable oils.

In addition to the active compounds and excipients, the pharmaceutical preparations can also contain additives, such as, for example, fillers, extenders, disintegrants, binders, lubricants, wetting agents, stabilisers, emulsifiers, preservatives, sweeteners, colorants, flavourings or aromatisers, buffer substances, and also solvents or solubilisers or agents for achieving a depot effect, as well as salts for changing the osmotic pressure, coating agents or antioxidants. They can also contain two or more compounds of the general formula I or their pharmacologically acceptable acid addition salts and additionally other therapeutically active substances.

Other therapeutically active substances of this type are, for example: β-receptor blockers, such as, for example, propranolol, pindolol, metoprolol; vasodilators, such as, for example, carbocromen; tranquillizers, such as, for example, barbituric acid derivatives, 1,4-benzodiacepines and meprobamate; diuretics, such as, for example, chlorothiazide; cardiotonic agents, such as, for example, digitalis preparations; hypotensive agents, such as, for example, hydralazine, dihydralazine, ramipril, prazosin, clonidine, rauwolfia alkaloids; agents which reduce the fatty acid level in the blood, such as, for example, bězafibrate, fenofibrate; and agents for thrombosis prophylaxis, such as, for example, phenprocoumon.

The compounds of the general formula I, their pharmacologically acceptable acid addition salts and pharmaceutical preparations which contain the compounds of the general formula I or their pharmacologically acceptable acid addition salts as active compounds can be used in humans in the control or prevention of disorders of the cardiovascular system, for example as antihypertensive medicines in the various forms of high blood pressure, and in the control or prevention of angina pectoris, etc. Moreover, they can also be employed for the treatment of erectile dysfunctions. The dose can vary within wide limits and is to be adapted to the individual conditions in each individual case. In general, in the case of oral administration a daily dose of about 0.5 to 100 mg, preferably 1 to 20 mg, is adequate per human individual. In the case of other administration forms, the daily dose, because of the good absorption of the active compounds, is also in similar ranges of amounts, i.e. in general also 0.5 to 100 mg/human. The daily dose is normally divided into several, for example 2 to 4, part administrations.

EXAMPLES

1. N-Methyl-4-phenyl-1,2,5-oxadiazole-3-carboxamide-2-oxide and N-methyl-3-phenyl-1,2,5-oxadiazole-4-carboxamide-2-oxide a) Somewhat more than the equimolar amount of methylamine (2 g) is passed into a mixture of 9.5 of 3-phenyl-4-hydroximino-isoxazol-5-one and 50 ml of methanol. The mixture is stirred at room temperature for 48 hours and then in an ice-bath. The precipitate is then filtered off with suction, washed with a little methanol and dried.

Yield: 8.7 g of N-methyl-3-phenyl-2,3-dihydroximinopropionamide M.p.: 149° C. (dec.)

b) 21 ml of a 14% strength sodium hypochlorite solution are added dropwise to an ice-cooled solution of 7.2 g of the compound according to a) in 23 ml of 2N sodium hydroxide solution. After 15 minutes, the precipitate is filtered off with suction, washed with water, dried and separated by column chromatography (silica gel; cyclohexane:ethyl acetate=8:2). 2.9 g of 4-phenyl compound result having an m.p. of 117–9° C. and 2.4 g of the 3-phenyl compound having an m.p. of 134–6° C.

2. N-(2-Diethylaminoethyl)-4-phenyl-1,2,5-oxadiazole-3-carboxamide-2-oxide and N-(2-diethylaminoethyl)-3-phenyl-1,2,5-oxadioazole-4-carboxamide-2-oxide a) N-(2-Diethylaminoethyl)-3-phenyl-2,3-dihydroximinopropionamide is prepared analogously to the information in Example 1a). M.p.: 157–8 (dec.).

b) 25 ml of a 14% strength sodium hypochlorite solution are added dropwise to an ice-cooled solution of 10.7 g of the compound according to a) in 35 ml of 2N sodium hydroxide solution. After 20 minutes, the oily product mixture is extracted with ethyl acetate and, after concentrating in vacuo, separated by column chromatography (silica gel; cyclohexane:acetone=7:3). In this way, 4.5 g of the 4-phenyl compound and 2.9 g of the 3-phenyl compound are obtained, in each case as an oil.

The following can be obtained analogously to Examples 1 and 2;

3. N-(2-Hydroxyethyl)-3-phenyl-1,2,5-oxadiazole-4-carboxamide-2-oxide (m.p.: 120°–121° C.) and N-(2-hydroxyethyl)-4-phenyl-1,2,5-oxadiazole-3-carboxamide-2-oxide (m.p.: 104°–106° C.) from N-(2-hydroxyethyl)-3-phenyl-2,3-dihydroximinopropionamide (m.p.: 179–81° C. (dec.)).

4. N-Methyl-3-(3,4-dimethoxyphenyl)-1,2,5-oxadiazole-4-carboxamide-2-oxide (m.p.: 156–8° C.) and N-methyl-4-(3,4-dimethoxyphenyl)-1,2,5-oxadiazole-3-carboxamide-2-oxide (m.p.: 145–8° C.) from N-methyl-3-(3,4-dimethoxyphenyl)-2,3-dihydroximinopropionamide (m.p.: 136° C. (dec.)).

5. N-Butyl-3-phenyl-1,2,5-oxadiazole-4-carboxamide-2-oxide (oil) and N-butyl-4-phenyl-1,2,5-oxadiazole-3-carboxamide-2-oxide (m.p.: 76–8° C.) from N-butyl-3-phenyl-2,3-dihydroximinopropionamide (oil).

6. N-(3-Diethylaminopropyl)-3-phenyl-1,2,5-oxadiazole-4-carboxamide-2-oxide (oil) and N-(3-diethylaminopropyl)-4-phenyl-1,2,5-oxadiazole-3-carboxamide-2-oxide (oil) form N-(3-diethylaminopropyl)-3-phenyl-2,3-dihydroximinopropionamide (m.p.: 157° C. (dec.)).

The compounds of the following table can additionally be obtained:
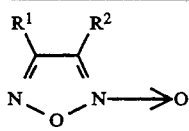
| | R¹ | R² | M.p. |
|---|---|---|---|
| 7a | 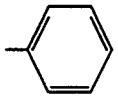 | —CONHCH₂— 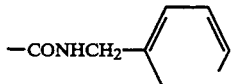 | 121–3° C. |
| 7b | —CONHCH₂— 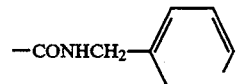 | 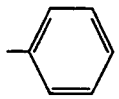 | 148–9° C. |
| 8a | 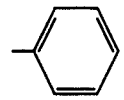 | —CONH—(CH₂)₃—N 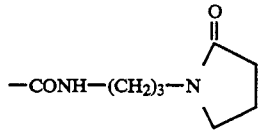 | 109–10° C. |
| 8b | —CONH(CH₂)₃—N 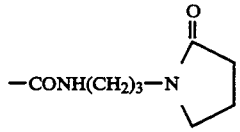 | 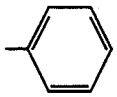 | 94–7° C. |
| 9a | 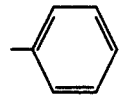 | —CONH—(CH₂)₃—N 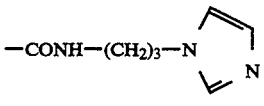 | 111–3° C. |
| 9b | —CONH—(CH₂)₃—N 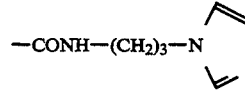 | 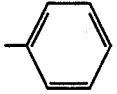 | 156–8° C. |
| 10a | 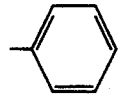 | —CONHCH₂—CO—NH₂ | 213–4° C. |
| 10b | —CONHCH₂—CO—NH₂ |  | 204–6° C. |
| 11a | 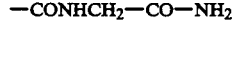 | —CON 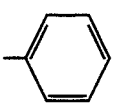 N—CH₃ | 106–8° C. |
| 11b | —CON 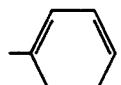 N—CH₃ | 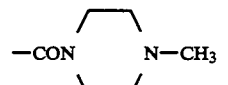 | 123–5° C. |
| 12a | 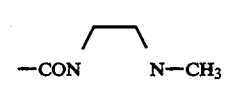 | —CONH(CH₂)₂N(iPr)₂.HCl | 128–30° C. |

-continued furazan N-oxide core structure with R¹ and R² substituents

| | R¹ | R² | M.p. |
|---|---|---|---|
| 12b | —CONH(CH₂)₂N(iPr)₂·HCl | phenyl | from 82° C. dec. |
| 13a | 3,4-dimethoxyphenyl | —CONH(CH₂)₂N(iPr)₂ | 125–6° C. |
| 13b | —CONH(CH₂)₂N(iPr)₂ | 3,4-dimethoxyphenyl | 132–5° C. |
| 14a | phenyl | —CONH—CH₂-(4-pyridyl) | 115–6° C. |
| 14b | —CONH—CH₂-(4-pyridyl) | phenyl | 144–5° C. |
| 15a | phenyl | —CONH(CH₂)₂-(imidazolyl) | 133–5° C. |
| 15b | —CONH(CH₂)₂-(imidazolyl) | phenyl | 163–5° C. |
| 16a | phenyl | —CONH(CH₂)₂-phenyl | 77–9° C. |
| 16b | —CONH(CH₂)₂-phenyl | phenyl | 110–1° C. |
| 17a | phenyl | —CONH(CH₂)₂—NH₂ | Oil |
| 17b | —CONH(CH₂)₂—NH₂ | phenyl | Oil |

-continued

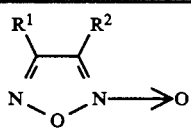

| | R¹ | R² | M.p. |
|---|---|---|---|
| 18a | ![4-nitrophenyl] | —CONH—(CH₂)₂—N(iPr)₂ | 114–5° C. |
| 18b | —CONH(CH₂)₂—N(iPr)₂ | ![4-nitrophenyl] | 79–81° C. |
| 19a | ![phenyl] | —CONH(CH₂)₃NMe₂ | Oil |
| 19b | —CONH(CH₂)₃NMe₂ | ![phenyl] | 83–5° C. |

20. 3-(3,4-Dimethoxiphenyl)-N-(pyrid-3-yl-methyl)-1,2,5-oxadiazole-4-carbonamide-2-oxide m.p.: 153°–155° C.
21. 4-(3,4-Dimethoxiphenyl)-N-(pyrid-3-yl-methyl)-1,2,5-oxadiazole-3-carbonamide-2-oxide m.p.: 111°–114° C.
22. 4-(4-Nitrophenyl)-N-(2-diisopropylamino-ethyl)-1,2,5-oxadiazole-3-carbonamide-2-oxide m.p.: 114°–115° C.

The following values were obtained:

| Compound | IC₅₀ (mol/l) |
|---|---|
| 1a | $1 \times 10^{-6}$ |
| 4a | $5 \times 10^{-6}$ |
| 5a | $7 \times 10^{-7}$ |
| 6a | $4 \times 10^{-7}$ |
| 7a | $3 \times 10^{-7}$ |
| 7b | $2 \times 10^{-6}$ |
| 10a | $1 \times 10^{-6}$ |
| 12b | $2 \times 10^{-6}$ |
| 13a | $3 \times 10^{-7}$ |
| 14a | $5 \times 10^{-7}$ |
| 14b | $1 \times 1.^{-6}$ |
| Molsidomine (comparison) | $3 \times 10^{-4}$ |
| Isosorbide-5-mononitrate (comparison) | $>1 \times 10^{-4}$ |

The pharmacological action of the compounds of the general formula I was determined by a modified method of Godfraind and Kaba (Arch. Int. Pharmacodyn. Ther. 196, (Suppl) 35 to 49, 1972) and by Schüman et al (Naunyn-Schmiedeberg's Arch. Pharmacol. 289, 409 to 418, 1975). In this method, spiral strips of the pulmonary artery of the guinea-pig are depolarised with 40 mmol/l of potassium after equilibration in calcium-free Tyrode solution. An addition of 0.5 mmol/l of CaCl₂ then induces a contraction.

The relaxing action of the test substance is determined by cumulative addition in ½ log 10 graded concentrations. From the concentration-action curve (abscissa: —log mol/l test substance, ordinate: % inhibition of the maximum contraction, average value of 4 to 6 vessel strips), the concentration of the test substance is determined which inhibits the contraction by 50% (=IC₅₀, mol/l).

It is to be understood that the above described embodiments of the invention are illustrative only, and that modifications thereof may occur to those skilled in the art. Accordingly, this invention is not to be regarded as limited to the embodiments disclosed herein, but is to be limited only as defined by the appended claims.

We claim:

1. Phenyl-1,2,5-oxadiazolecarboxamide-2-oxides of the formula I

 (I)

in which one of the radicals R¹ and R² represents

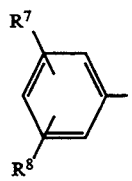

and the other represents

where

R³ denotes (C₁-C₅)-alkyl, (C₅-C₇)-cycloalkyl, —(CH₂)ₙ—NR⁵R⁶, —(CH₂)ₙ—OR⁵, —(CH₂)ₘ—COOR⁵, —CH(Alk)—COOR⁵, —(CH₂)ₘ—CONR⁵R⁶, —(Alk)—CONR⁵R⁶,

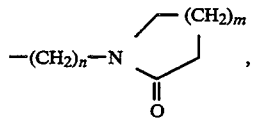

—(CH₂)ₘ-aryl or —(CH₂)ₘ-heteroaryl and R⁴ denotes R³ or hydrogen or R³ and R⁴, together with the nitrogen atom bonding them, form a heterocycle;

R⁵ and R⁶ independently of one another denote hydrogen, (C₁-C₆)-alkyl, (C₅-C₇)-cycloalkyl, benzyl or phenethyl;

Alk denotes (C₁-C₆)-alkyl;

n represents 2, 3 or 4 and m represents 1, 2 or 3; and

R⁷ and R⁸ independently of one another denote hydrogen, (C₁-C₄)-alkyl, (C₁-C₄)-alkoxy, fluorine, chlorine, bromine, nitro or trifluoromethyl;

and their pharmacologically acceptable acid addition compounds.

2. Phenyl-1,2,5-oxadiazolecarboxamide-2-oxides according to claim 1, characterised in that R³ denotes (C₁-C₅)-alkyl and R⁴ denotes hydrogen.

3. Phenyl-1,2,5-oxadiazolecarboxamide-2-oxides according to claim 1, characterised in that R³ denotes —(CH₂)ₙN(C₁-C₆)-alkyl)₂ and R⁴ denotes hydrogen.

4. Phenyl-1,2,5-oxadiazolecarboxamide-2-oxides according to claim 1, characterised in that

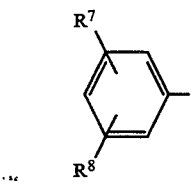

representing R¹ or R² is unsubstituted phenyl.

5. Phenyl-1,2,5-oxadiazolecarboxamide-2-oxides according to claim 1, characterised in that R³ denotes —(CH₂)ₙN((C₁-C₆)-alkyl)₂ and R⁴, R⁷ and R⁸ denote hydrogen.

6. Process for the treatment of disorders of the cardiovascular system, which comprises administering to a patient in need thereof effective amounts of Phenyl-1,2,5-oxadiazolecarboxamide-2-oxides of the formula I

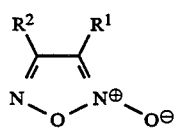

in which one of the radicals R¹ and R² represents

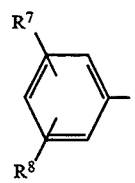

and the other represents

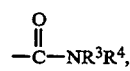

where

R³ denotes (C₁-C₆)-alkyl, (C₅-C₇)-cycloalkyl, —(CH₂)ₙ—NR⁵R⁶, —(CH₂)ₙ—OR⁵, —(CH₂)ₘ—COOR⁵, —CH(Alk)—COOR⁵, —(CH₂)ₘ—CONR⁵R⁶, —CH(Alk)—CONR⁵R⁶,

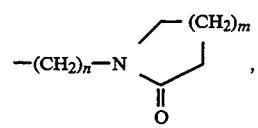

—(CH₂)ₘ-aryl or —(CH₂)ₘ-heteroaryl and R⁴ denotes R³ or hydrogen, or R³ and R⁴, together with the nitrogen atom bonding them, form a heterocycle;

R⁵ and R⁶ independently of one another denote hydrogen, (C₁-C₆)-alkyl, (C₅-C₇)-cycloalkyl, benzyl or phenethyl;

Alk denotes (C₁-C₆)-alkyl;

n represents 2, 3 or 4 and m represents 1, 2 or 3; and

R⁷ and R⁸ independently of one another denote hydrogen, (C₁-C₄)-alkyl, (C₁-C₄)-alkoxy, fluorine, chlorine, bromine, nitro or trifluoromethyl; and their pharmacologically acceptable acid addition compounds.

7. Process for the treatment of erectile dysfunctions, which comprises administering to a patient in need thereof effective amounts of Phenyl-1,2,5-oxadiazolecarboxamide-2-oxides of the formula I

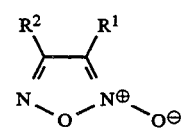

in which one of the radicals R¹ and R² represents

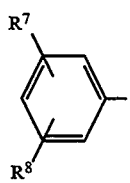

and the other represents

where $R^3$ denotes $(C_1-C_6)$-alkyl, $(C_5-C_7)$-cycloalkyl, —$(CH_2)_n$—$NR^5R^6$, —$(CH_2)_n$—$OR^5$, —$(CH_2)_m$—$COOR^5$, —CH(Alk)—$COOR^5$, —$(CH_2)_m$—$CONR^5R^6$, —CH(Alk)—$CONR^5R^6$,

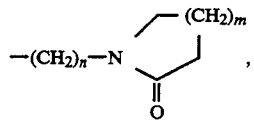

—$(CH_2)_m$-aryl or —$(CH_2)_m$-heteroaryl and $R^4$ denotes $R^3$ or hydrogen, $R^3$ and $R^4$, together with the nitrogen atom bonding them, form a heterocycle;

$R^5$ and $R^6$ independently of one another denote hydrogen, $(C_1-C_6)$-alkyl, $(C_5-C_7)$-cycloalkyl, benzyl or phenethyl;

Alk denotes $(C_1-C_6)$-alkyl;

n represents 2, 3 or 4 and m represents 1, 2 or 3; and $R^7$ and $R^8$ independently of one another denote hydrogen, $(C_1-C_4)$-alkyl, $(C_1-C_4)$-alkoxy, fluorine, chlorine, bromine, nitro or trifluoromethyl; and their pharmacologically acceptable acid addition compounds.

8. Pharmaceutical preparation, characterized in that it contains an effective amount, between about 0.5 and 100 mg, of a phenyl-1,2,5-oxidiazolecarboxamide-2-oxide of the formula

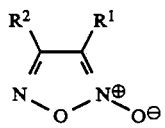

in which one of the radicals $R^1$ and $R^2$ represents

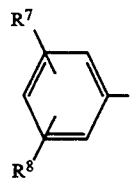

and the other represents

where $R^3$ denotes $(C_1-C_6)$-alkyl, $(C_5-C_7)$-cycloalkyl, —$(CH_2)_n$—$NR^5R^6$, —$(CH_2)_n$—$OR^5$, —$(CH_2)_m$—$COOR^5$, —CH(Alk)—$COOR^5$, —$(CH_2)_m$—$CONR^5R^6$, —CH(Alk)—$CONR^5R^6$,

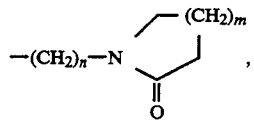

—$(CH_2)_m$-aryl or —$(CH_2)_m$-heteroaryl, and $R^4$ denotes $R^3$ or hydrogen, or $R^3$ and $R^4$, together with the nitrogen atom bonding them, form a heterocycle;

$R^5$ and $R^6$ independently of one another denote hydrogen, $(C_1-C_6)$-alkyl, $(C_5-C_7)$-cycloalkyl, benzyl or phenethyl;

Alk denotes $(C_1-C_6)$-alkyl;

n represents 2, 3 or 4 and m represents 1, 2 or 3; and $R^7$ and $R^8$ independently of one another denote hydrogen, $(C_1-C_4)$-alkyl, $(C_1-C_4)$-alkoxy, fluorine, chlorine, bromine, nitro or trifluoromethyl or a pharmacologically acceptable acid addition salt thereof as active compound together with pharmaceutically acceptable excipient and additives and, optionally, one or more other pharmacological active compounds.

* * * * *